(12) United States Patent
Holman

(10) Patent No.: US 11,287,254 B2
(45) Date of Patent: Mar. 29, 2022

(54) LOCALIZED DEFORMATION SENSOR

(71) Applicant: Tactual Labs Co., New York, NY (US)

(72) Inventor: David Holman, Toronto (CA)

(73) Assignee: Tactual Labs Co., New York, NY (US)

( * ) Notice: Subject to any disclaimer, the term of this patent is extended or adjusted under 35 U.S.C. 154(b) by 0 days.

(21) Appl. No.: 16/913,966

(22) Filed: Jun. 26, 2020

(65) Prior Publication Data
US 2020/0408515 A1 Dec. 31, 2020

Related U.S. Application Data

(60) Provisional application No. 62/866,970, filed on Jun. 26, 2019.

(51) Int. Cl.
| | |
|---|---|
| *G01B 15/06* | (2006.01) |
| *G01P 13/00* | (2006.01) |
| *G01B 7/287* | (2006.01) |
| *A61B 5/11* | (2006.01) |

(52) U.S. Cl.
CPC ............ *G01B 15/06* (2013.01); *G01B 7/287* (2013.01); *G01P 13/00* (2013.01); *A61B 5/11* (2013.01)

(58) Field of Classification Search
USPC .......................................................... 702/150
See application file for complete search history.

(56) References Cited

U.S. PATENT DOCUMENTS

| | | | | |
|---|---|---|---|---|
| 2011/0208444 | A1* | 8/2011 | Solinsky | A61B 5/1122 |
| | | | | 702/41 |
| 2016/0338644 | A1* | 11/2016 | Connor | A61B 5/1071 |
| 2017/0112391 | A1* | 4/2017 | Stivoric | A61B 5/0022 |
| 2017/0118838 | A1* | 4/2017 | Williams | H05K 3/32 |
| 2017/0156662 | A1* | 6/2017 | Goodall | G16H 50/30 |
| 2018/0338709 | A1* | 11/2018 | Krans | A61B 5/0022 |

* cited by examiner

*Primary Examiner* — Paul D Lee
(74) *Attorney, Agent, or Firm* — Adam Landa

(57) ABSTRACT

A sensing system is embedded into a fabric or material that conforms to a portion of a user's body. The fabric or material has transmitting antennas and receiving antennas placed thereon. Movement of the fabric or material with the transmitting and receiving antennas placed thereon are able to measure the changes in the signals received by the receiving antennas. Measurement of the changes are used to determine movement of and position of parts of the body within and/or distal to the fabric or material by determining localized pressure deformation to reconstruct volumetric changes.

20 Claims, 5 Drawing Sheets

LOCALIZED DEFORMATION SENSOR

This application claims the benefit of U.S. Provisional Application No. 62/866,970, filed Jun. 26, 2019, the contents of which are incorporated herein by reference. This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The disclosed systems relate in general to the field of sensing, and in particular to controls that are able to determine activity at various parts of the body from a localized sensor that is adapted to perform localized deformation sensing.

BRIEF DESCRIPTION OF THE DRAWINGS

The foregoing and other objects, features, and advantages of the disclosure will be apparent from the following more particular description of embodiments as illustrated in the accompanying drawings in which reference characters refer to the same parts throughout the various views. The drawings are not necessarily to scale, emphasis instead being placed upon illustrating principles of the disclosed embodiments.

DETAILED DESCRIPTION

Figure 1:
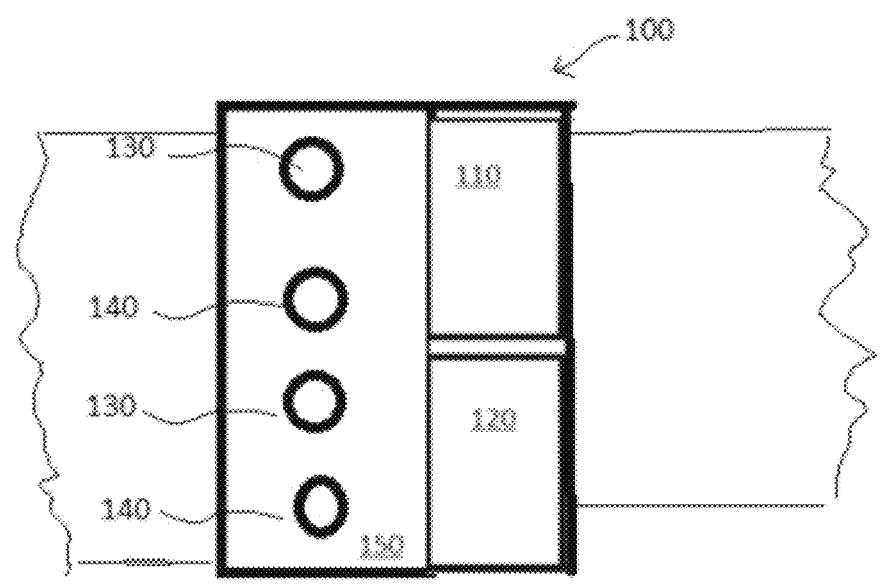
FIG. 1 shows a simplified diagram of a sensing system.

In various embodiments, the present disclosure is directed to sensing systems sensitive to determine movement based on localized deformation sensing.

The application employs principles used in fast multi-touch sensors and other interfaces disclosed in the following: U.S. Pat. Nos. 9,933,880; 9,019,224; 9,529,476; 9,811,214; 9,804,721; 9,710,113; and 9,158,411. Familiarity with the disclosure, concepts and nomenclature within these patents is presumed. The entire disclosures of those patents and the applications incorporated therein by reference are incorporated herein by reference. This application also employs principles used in fast multi-touch sensors and other interfaces disclosed in the following: U.S. patent application Ser. Nos. 15/162,240; 15/690,234; 15/195,675; 15/200,642; 15/821,677; 15/904,953; 15/905,465; 15/943,221; 62/540,458, 62/575,005, 62/621,117, 62/619,656 and PCT publication PCT/US2017/050547, familiarity with the disclosures, concepts and nomenclature therein is presumed. The entire disclosure of those applications and the applications incorporated therein by reference are incorporated herein by reference.

As used herein, and especially within the claims, ordinal terms such as first and second are not intended, in and of themselves, to imply sequence, time or uniqueness, but rather, are used to distinguish one claimed construct from another. In some uses where the context dictates, these terms may imply that the first and second are unique. For example, where an event occurs at a first time, and another event occurs at a second time, there is no intended implication that the first time occurs before the second time, after the second time or simultaneously with the second time. However, where the further limitation that the second time is after the first time is presented in the claim, the context would require reading the first time and the second time to be unique times. Similarly, where the context so dictates or permits, ordinal terms are intended to be broadly construed so that the two identified claim constructs can be of the same characteristic or of different characteristics. Thus, for example, a first and a second frequency, absent further limitation, could be the same frequency, e.g., the first frequency being 10 Mhz and the second frequency being 10 Mhz; or could be different frequencies, e.g., the first frequency being 10 Mhz and the second frequency being 11 Mhz. Context may dictate otherwise, for example, where a first and a second frequency are further limited to being frequency orthogonal to each other, in which case, they could not be the same frequency.

Certain principles of a fast multi-touch (FMT) sensor have been disclosed in the patent applications discussed above. Orthogonal signals may be transmitted into a plurality of transmitting antennas (or conductors) and information may be received by receivers attached to a plurality of receiving antennas (or conductors). In an embodiment, receivers "sample" the signal present on the receiving antennas (or conductors) during a sampling period ($\tau$). In an embodiment, signal (e.g., the sampled signal) is then analyzed by a signal processor to identify touch events (including, e.g., actual touch, near touch, hover and farther away events that cause a change in coupling between a transmitting antenna (or conductor) and receiving antennas (or conductor)). In an embodiment, one or more transmitting antennas (or conductors) can move with respect to one or more receiving antennas (or conductors), and such movement causes a change of coupling between at least one of the transmitting antennas (or conductors) and at least one of the receiving antennas (or conductors). In an embodiment, one or more transmitting antennas (or conductors) are relatively fixed with respect to one or more receiving antennas (or conductors), and the interaction of the signal and/or signals transmitted with environmental factors causes a change of coupling between at least one of the transmitting antennas (or conductors) and at least one of the receiving antennas (or conductors). The transmitting antennas (or conductors) and receiving antennas (or conductors) may be organized in a variety of configurations, including, e.g., a matrix where the crossing points form nodes, and interactions are detected by processing of received signals. In an embodiment where the orthogonal signals are frequency orthogonal, spacing between the orthogonal frequencies, $\Delta f$, is at least the reciprocal of the measurement period $\tau$, the measurement period $\tau$ being equal to the period during which the column conductors are sampled. Thus, in an embodiment, the received at a column conductor may be measured for one millisecond ($\tau$) using frequency spacing ($\Delta f$) of one kilohertz (i.e., $\Delta f=1/\tau$).

In an embodiment, the signal processor of a mixed signal integrated circuit (or a downstream component or software) is adapted to determine at least one value representing each frequency orthogonal signal transmitted to (or present on) a row conductor (or antenna). In an embodiment, the signal processor of the mixed signal integrated circuit (or a downstream component or software) performs a Fourier transform on the signals present on a receive antenna (or conductor). In an embodiment, the mixed signal integrated circuit is adapted to digitize received signals. In an embodiment, the mixed signal integrated circuit (or a downstream component or software) is adapted to digitize the signals present on the receive conductor or antenna and perform a discrete Fourier transform (DFT) on the digitized information. In an embodiment, the mixed signal integrated circuit (or a downstream component or software) is adapted to digitize the signals present on the received conductor or antenna and perform a Fast Fourier transform (FFT) on the digitized information—an FFT being one type of discrete Fourier transform.

It will be apparent to a person of skill in the art in view of this disclosure that a DFT, in essence, treats the sequence of digital samples (e.g., window) taken during a sampling period (e.g., integration period) as though it repeats. As a consequence, signals that are not center frequencies (i.e., not integer multiples of the reciprocal of the integration period (which reciprocal defines the minimum frequency spacing)), may have relatively nominal, but unintended consequence of contributing small values into other DFT bins. Thus, it will also be apparent to a person of skill in the art in view of this disclosure that the term orthogonal as used herein is not "violated" by such small contributions. In other words, as the term frequency orthogonal is used herein, two signals are considered frequency orthogonal if substantially all of the contribution of one signal to the DFT bins is made to different DFT bins than substantially all of the contribution of the other signal.

When sampling, in an embodiment, received signals are sampled at at least 1 MHz. In an embodiment, received signals are sampled at at least 2 MHz. In an embodiment, received signals are sampled at at least 4 Mhz. In an embodiment, received signals are sampled at 4.096 Mhz. In an embodiment, received signals are sampled at more than 4 MHz. To achieve kHz sampling, for example, 4096 samples may be taken at 4.096 MHz. In such an embodiment, the integration period is 1 millisecond, which per the constraint that the frequency spacing should be greater than or equal to the reciprocal of the integration period provides a minimum frequency spacing of 1 KHz. (It will be apparent to one of skill in the art in view of this disclosure that taking 4096 samples at e.g., 4 MHz would yield an integration period slightly longer than a millisecond, and not achieving kHz sampling, and a minimum frequency spacing of 976.5625 Hz.) In an embodiment, the frequency spacing is equal to the reciprocal of the integration period. In such an embodiment, the maximum frequency of a frequency-orthogonal signal range should be less than 2 MHz. In such an embodiment, the practical maximum frequency of a frequency-orthogonal signal range should be less than about 40% of the sampling rate, or about 1.6 MHz. In an embodiment, a DFT (which could be an FFT) is used to transform the digitized received signals into bins of information, each reflecting the frequency of a frequency-orthogonal signal transmitted which may have been transmitted by the transmitting antenna. In an embodiment 2048 bins correspond to frequencies from 1 KHz to about 2 MHz. It will be apparent to a person of skill in the art in view of this disclosure that these examples are simply that, exemplary. Depending on the needs of a system, and subject to the constraints described above, the sample rate may be increased or decreased, the integration period may be adjusted, the frequency range may be adjusted, etc.

In an embodiment, a DFT (which can be an FFT) output comprises a bin for each frequency orthogonal signal that is transmitted. In an embodiment, each DFT (which can be an FFT) bin comprises an in-phase (I) and quadrature (Q) component. In an embodiment, the sum of the squares of the I and Q components is used as measures corresponding to signal strength for that bin. In an embodiment, the square root of the sum of the squares of the I and Q components is used as measure corresponding to signal strength for that bin. It will be apparent to a person of skill in the art in view of this disclosure that a measure corresponding to the signal strength for a bin could be used as a measure related to activity, touch events, etc. In other words, the measure corresponding to signal strength in a given bin would change as a result of some activity proximate to the sensors, such as a touch event.

The sensing apparatuses discussed herein use transmitting and receiving antennas (also referred to herein as conductors, row conductors, column conductors, transmitting conductors, or receiving conductors). However, it should be understood that whether the transmitting antennas or receiving antennas are functioning as a transmitter, a receiver, or both depends on context and the embodiment. In an embodiment, the transmitters and receivers for all or any combination of the arrangements are operatively connected to a single integrated circuit capable of transmitting and receiving the required signals. In an embodiment, the transmitters and receivers are each operatively connected to a different integrated circuit capable of transmitting and receiving the required signals, respectively. In an embodiment, the transmitters and receivers for all or any combination of the patterns may be operatively connected to a group of integrated circuits, each capable of transmitting and receiving the required signals, and together sharing information necessary to such multiple IC configuration. In an embodiment, where the capacity of the integrated circuit (i.e., the number of transmit and receive channels) and the requirements of the patterns (i.e., the number of transmit and receive channels) permit, all of the transmitters and receivers for all of the multiple patterns used by a controller are operated by a common integrated circuit, or by a group of integrated circuits that have communications therebetween. In an embodiment, where the number of transmit or receive channels requires the use of multiple integrated circuits, the information from each circuit is combined in a separate system. In an embodiment, the separate system comprises a GPU and software for signal processing.

In an embodiment, the mixed signal integrated circuit is adapted to generate one or more signals and send the signals to the transmitting antennas via the transmitter. In an embodiment, the mixed signal integrated circuit is adapted to generate a plurality of frequency orthogonal signals and send the plurality of frequency orthogonal signals to the transmitting antennas. In an embodiment, the mixed signal integrated circuit is adapted to generate a plurality of frequency orthogonal signals and one or more of the plurality of frequency orthogonal signals to each of a plurality of transmit antennas. In an embodiment, the frequency orthogonal signals are in the range from DC up to about 2.5 GHz. In an embodiment, the frequency orthogonal signals are in the range from DC up to about 1.6 MHz. In an embodiment, the frequency orthogonal signals are in the range from 50 KHz to 200 KHz. The frequency spacing between the frequency orthogonal signals should be greater than or equal to the reciprocal of the integration period (i.e., the sampling period).

In an embodiment, the mixed signal integrated circuit (or a downstream component or software) is adapted to determine at least one value representing each frequency orthogonal signal transmitted by a transmitting antenna. In an embodiment, the mixed signal integrated circuit (or a downstream component or software) performs a Fourier transform on received signals. In an embodiment, the mixed signal integrated circuit is adapted to digitize received signals. In an embodiment, the mixed signal integrated circuit (or a downstream component or software) is adapted to digitize received signals and perform a discrete Fourier transform (DFT) on the digitized information. In an embodiment, the mixed signal integrated circuit (or a downstream component or software) is adapted to digitize received signals and perform a Fast Fourier transform (FFT) on the digitized information.

Turning to FIG. 1, a simplified diagram is shown that sets forth an example of a sensing system 100, which is incorporated into wearable 150. In FIG. 1, the wearable 150 is placed on a wrist. In an embodiment, a mixed signal integrated circuit with signal processing capabilities comprises a transmitter 110, and a receiver 120. In an embodiment, an analog front end comprising a transmitter (or multiple transmitters) and a receiver (or multiple receivers) is used to send and receive signals instead of the mixed signal integrated circuit. In such an embodiment, the analog front end provides a digital interface to signal generating and signal processing circuits and/or software. In an embodiment, the mixed signal integrated circuit is adapted to generate one or more signals and send the signals to the transmitting antenna 130 (also referred to as an electrode or conductor) via the transmitter 110. In an embodiment, the mixed signal integrated circuit 100 is adapted to generate a plurality of frequency-orthogonal signals and send the plurality of frequency-orthogonal signals to the transmitting antennas 130.

The transmitter 110 is conductively coupled to transmitting antennas 130, and the receiver 120 is operably connected to receiving antennas 140 (also referred to herein as conductors or electrodes). The transmitting antenna 130 is supported on the wearable 150 that is worn on a body part. It will be apparent to a person of skill in the art in view of this disclosure that the transmitting antennas and receiving antennas are arbitrarily assigned, and the transmitting antenna 130 can be used on the receive side, while the receiving antenna 140 can be used as the transmit side. It will also be apparent to a person of skill in the art in view of this disclosure that signal processor, transmitter and receiver may be implemented on separate circuits. It will be apparent to a person of skill in the art in view of this disclosure that the transmitter and receivers may support more than one antenna. In an embodiment, a plurality of transmitting antennas 130 and/or a plurality of receiving antennas 140 are employed. Measurements of signals received by the receiving antennas 140 are used in order to determine information regarding the position and movement of body parts.

Further discussion regarding the implementation of the transmitting antennas (or conductors) and receiving antennas (or conductors) in association with wearables can be found in U.S. patent application Ser. No. 15/926,478, U.S. patent application Ser. No. 15/904,953, U.S. patent application Ser. No. 16/383,090 and U.S. patent application Ser. No. 16/383,996, the contents of all of the aforementioned applications incorporated herein by reference.

Figure 2:
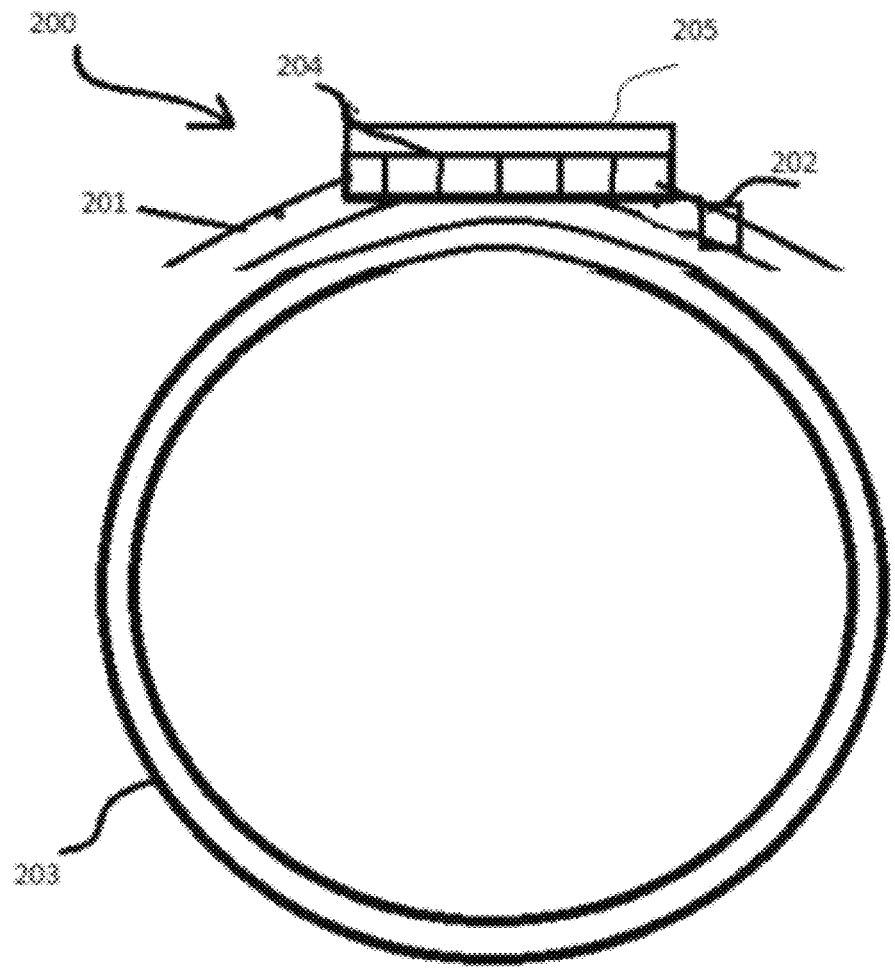
FIG. 2 is a diagram of a sensing system.

FIG. 2 is a diagram showing an embodiment of a sensing system 200 located proximate to a wrist area 203. Sensing system 200 is operably attached to a body at a location where information regarding the activity of a particular muscle or muscle grouping is able to be determined. In FIG. 2, sensing system 200 is connected to the wrist area 203 via the use of a band 201. In the arrangement depicted in FIG. 2 the activity of muscles that control motion of the hand are able to be detected. However, it should be understood, and, as discussed below, sensing systems may be operably connected to other parts of the body and/or operably connected to the body using mechanisms other than bands. The sensing system 200 comprises receiving antennas 204 (antennas are also referred to as conductors or electrodes) that are operably connected to a processor (not shown). The receiving antennas 204 are located within a housing 205. The housing 205 is operably attached to the band 201.

When the sensing system 200 is worn, the receiving antennas 204 are adapted to be located above the surface of the skin of the wrist area 203. In the embodiment, shown in FIG. 2, each of the receiving antennas 204 are located at substantially the same distance from the surface of the wrist area 203 in a direction normal to the surface of the wrist area 203. The receiving antennas 204 may be separated from the surface of the wrist area 203 by material formed from the housing 205. In an embodiment, the band 201 separates the receiving antennas 204 from the surface of the wrist area 203. In an embodiment, a layer of material other than the band separates the receiving antennas from the surface of the skin. In an embodiment, a housing separates the receiving antenna or receiving antennas from the surface of the skin. In an embodiment, multiple layers of material separate the receiving antenna or receiving antennas from the surface of the skin. In an embodiment, a receiving antenna or receiving antennas are placed proximate to the surface of the skin without any intervening layers. In an embodiment, a receiving antenna or receiving antennas are placed on the surface of the skin.

When receiving antennas 204 are located distally from the surface of the skin there is less likelihood of factors such as sweat, skin chemistry, texture, biological factors, etc. from interfering with the measurements. In an embodiment, the receiving antennas 204 are adapted to be positioned about 2 mm from the surface of the skin. In an embodiment, the receiving antennas 204 are adapted to be positioned about 1 mm from the surface of the skin. In an embodiment, the receiving antennas 204 are adapted to be positioned about 3 mm from the surface of the skin. In an embodiment, the receiving antennas 204 are adapted to be positioned about 4 mm from the surface of the skin. In an embodiment, the receiving antennas 204 are adapted to be positioned about 5 mm from the surface of the skin. In an embodiment, some receiving antennas are positioned at different distances from the surface of the skin. For example, one grouping of receiving antennas is positioned at 1 mm from the surface of the skin, while another grouping of receiving antennas is positioned at 2 mm from the surface of the skin. In an embodiment, each of the receiving antennas are positioned at a different distance from the surface of the skin. Generally, as the receiving antennas 204 approach, or are located in proximity to the surface of the skin, the magnitude of the infused signal received from the skin increases. Other factors that impact the reception of infused signal by the receiving antennas are the geometry of the receiving antennas and size of the receiving antennas.

The sensing system 200 also comprises transmitting antenna 202 (also referred to as a conductor or electrode). While a single transmitting antenna 202 is shown, more than one transmitting antenna may be used in the sensing system 200. More transmitting antennas can provide additional sources of signal that when measured and processed can provide additional information regarding the activity of muscles. The transmitting antenna 202 is adapted to infuse a signal into the user of the sensing system 200. The transmitting antenna 202 is operably connected to the band 201 and is located sufficiently proximate to the user so as to effectively transmit signal into the user so that the signal is able to be carried by the user. In an embodiment, the band 201 separates the transmitting antenna 202 from the surface of the wrist area 203. In an embodiment, a layer of material other than the band separates a transmitting antenna or transmitting antennas from the surface of the skin. In an embodiment, a housing separates the transmitting antenna or transmitting antennas from the surface of the skin. In an embodiment, multiple layers of material separate a transmitting antenna or transmitting antennas from the surface of the skin. In an embodiment, a transmitting antenna or transmitting antennas are placed proximate to the surface of the skin without any intervening layers. In an embodiment, a transmitting antenna or transmitting antennas are placed on the surface of the skin. The distance of the transmitting antenna from the surface of the skin or whether the transmitting antenna is located on the skin may be determined by factors such as signal strength and body chemistry.

In FIG. 2, the transmitting antenna 202 is shown located distally from the receiving antennas 204, however it should be understood that the transmitting antenna 202 may be located at various distances from the respective receiving antennas 202. The proximity of the transmitting antenna 202 to a receiving antenna 204 may impact the measurements of the signal received by the receiving antennas 204. It should also be understood that the roles of the transmitting antenna and the receiving antennas may switch or alternate in some embodiments, with the transmitting antenna functioning as receiving antenna and the receiving antennas functioning as transmitting antennas.

In FIG. 2, a transmitting antenna 202 is shown that infuses a signal to a user of the sensing system 200. In an embodiment, more than one transmitting antenna infuses signals to a user. In an embodiment, more than one transmitting antenna infuses signals to a user wherein each of the transmitting antennas infuses a signal that is orthogonal from each other signal transmitted to the user. In an embodiment, one transmitting antenna infuses more than one signal to a user wherein each of the signals transmitted to the user is orthogonal with respect to each other signal transmitted to the user. By using more transmitted signals potentially more information regarding the location being measured can be obtained.

While the transmitting antenna 202 is shown located on the band 203, it should be understood that the transmitting antenna 202 does not have to be located on the band 203 or necessarily proximate to the band 201. In an embodiment the transmitting antenna or antennas are located on a wearable located elsewhere on the body. In an embodiment, the transmitting antenna or antennas are located proximate to another hand of the user. In an embodiment the transmitting antenna or antennas are located on a ring worn by the user. In an embodiment the transmitting antenna or antennas are located on goggles or glasses located on the head. In an embodiment the transmitting antenna or antennas are located in an article of clothing worn by the user. In an embodiment the transmitting antenna or antennas are located on a token carried by the user.

In an embodiment, the transmitting antenna or antennas are located within the environment and signal is transmitted to the user upon being proximate to the transmitting antenna. In an embodiment, the transmitting antenna or antennas are located in a chair in which the user sits. In an embodiment, the transmitting antenna or antennas are located on the floor on which the user stands. In an embodiment, the transmitting antenna or antennas are located within a vehicle.

In FIG. 2 the geometry is set forth so that there is one transmitting antenna 202 and a plurality of receiving antennas 204. In an embodiment, the roles of the transmitting antenna and receiving antennas may be reversed or alternated. In an embodiment, a receiving antenna or receiving antennas are switched to perform the role of a transmitting antenna or transmitting antennas and the transmitting antenna or transmitting antennas are switched to perform the role of a receiving antenna or receiving antennas. By alternating roles of the antennas additional and different information may be obtained.

The embodiment shown and described in FIGS. 1 and 2 have been able to determine and distinguish movement and position of the fingers. While the embodiments discussed above and variations thereof are able to distinguish and determine position and movement of the hand, an elastic or neoprene type substrate that is formed into a wearable band or substrate can be used to provide information regarding other portions of the body. Furthermore, the extent of movement and information that can be ascertained by a localized deformable wearable is determined by the placement and extent of the information determined from the musculature and other movements of the body that can be discerned by measuring properties of the signals received by the receiving antennas. In an embodiment, the localized deformation sensing of the skin is used to reconstruct volumetric changes that occur in the area that is surrounded by the wearable. This is discussed further below.

Figure 3:
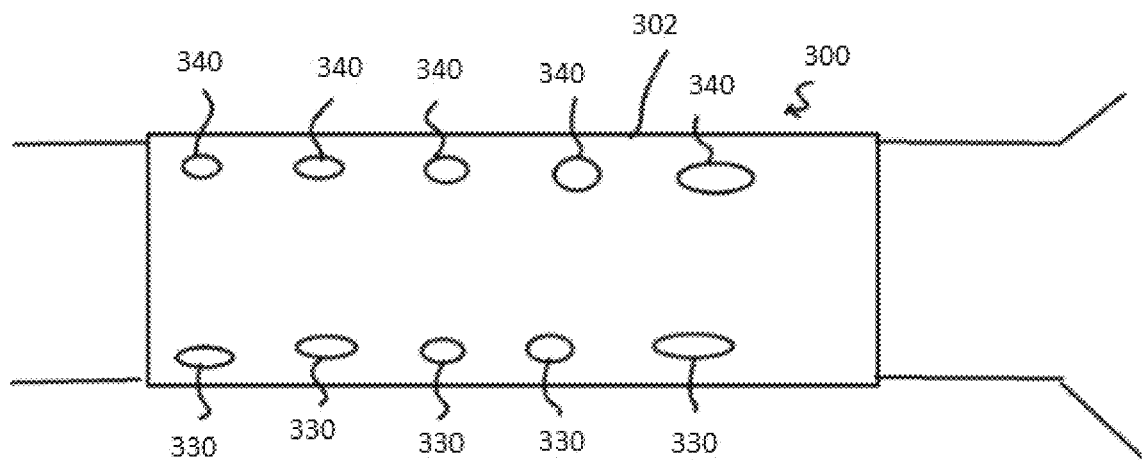
FIG. 3 is a diagram of a forearm wearable.

Turning to FIG. 3, a schematic diagram of a wearable 300 placed on a portion of a person's arm is shown. The wearable 300 comprises a substrate 302 that has transmitting antennas 330 and receiving antennas 340 embedded therein. In FIG. 3 the transmitting antennas 330 and the receiving antennas 340 are shown as disc shaped antennas. In an embodiment, the transmitting antennas and the receiving antennas may be formed as line shaped antennas. In an embodiment, the receiving antennas and the transmitting antennas may be formed in other arrangements that conform to the shape of the body part on which the wearable is to be located.

Returning to FIG. 3, the transmitting antennas 330 and the receiving antennas 340 are arranged on the substrate 302. In an embodiment, the substrate is formed of a neoprene material. In an embodiment, the substrate is formed of an elastic material. In an embodiment, the substrate is formed of a plastic material. In an embodiment, the substrate is formed of a woven material securely fitted to the body part. The transmitting antennas 330 and the receiving antennas 340 may be arranged in any arrangement sufficient to determine position and movement based on the measurement of the signals received at the receiving antennas. Additionally, the functions of the transmitting antennas and the receiving antennas may be switched, alternated or activated in certain patterns.

Still referring to FIG. 3, the transmitting antennas 330 transmit a plurality of signals. In an embodiment, the plurality of signals transmitted are frequency orthogonal with respect to each other signal that is transmitted at the same time. At least some of the frequency orthogonal signals are received at the receiving antennas 340. The signals that are received at the receiving antennas 340 are measured. The measurements of the signals of the received signals are used to determine position and movement of body parts. In an embodiment the amplitude of the received signals are measured. In an embodiment the phase of the received signals are measured. In an embodiment, the amplitude and the phase of the received signals are measured. In an embodiment, signals are injected or infused into the skin of the user in order to determine additional information regarding the user. In an embodiment, the properties of the signals that are measured are used to perform localized deformation sensing by using the measurements to reconstruct the volume.

Still referring to FIG. 3, the wearable 300 is located on the forearm. Movements of the hand and the shoulder are able to be determined by measurements of signals received. In an embodiment, machine learning is used to calibrate the wearable 300 so as to correlate specific movements within the forearm with particular movements of the body. In an embodiment, the determined movement of portions of the forearm are used to determine movements of a hand. In an embodiment, the movement of portions of the forearm are determined by movements of musculature. In an embodiment, the movement of portions of the forearm are determined by the movements of the circulatory system. In an embodiment, the movement of portions of the forearm are determined by the movements of the ligaments. In an embodiment, the movement of portions of the forearm are determined by the movements of the skin. In an embodiment, the movement of portions of the forearm are movement of the skin, ligaments, the circulatory system, the musculature or any combination thereof. In an embodiment, volumetric change of the forearm is used, such as localized deformation sensing (discussed below).

Figure 4:
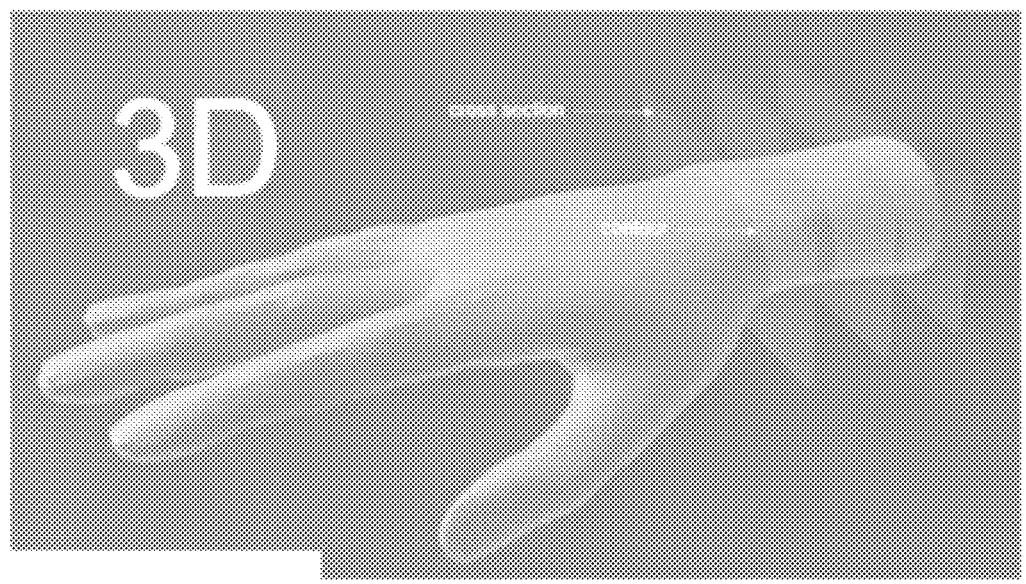
FIG. 4 is a view of localized deformation sensing of a forearm.
Figure 5:
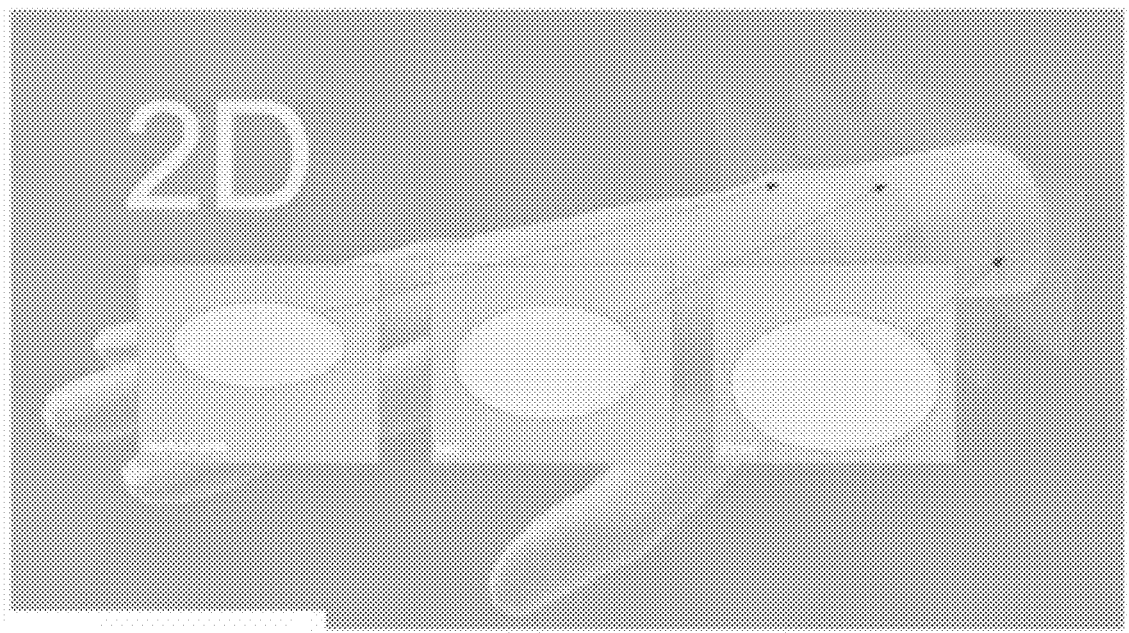
FIG. 5 is another view of localized deformation sensing of a forearm.
Figure 6:
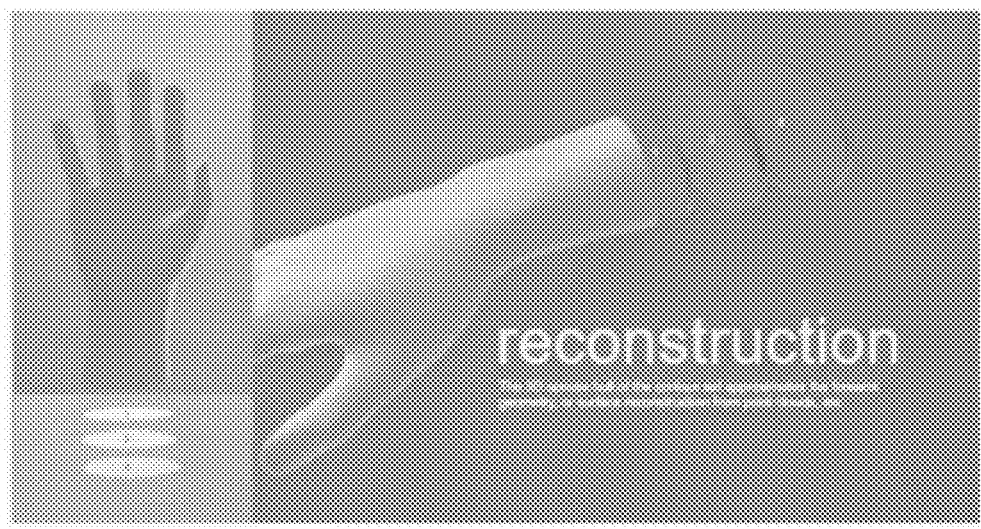
FIG. 6 is another view of localized deformation sensing of a forearm.

Referring to FIGS. 4-6, in an embodiment, "localized deformation sensing" is used for determining movements of portions of the body via the reconstruction of volumetric movements of portions of the body. Localized deformation sensing is a technique for surface reconstruction of three-dimensional geometries using sampling taken from the signals received. In particular, volumetric change of the forearm is constructed using dynamic cross-sectional contours. The contours are produced by sensing localized skin surface deformations that are orthogonal to the forearm axis. Given a set of contours measured at a known spacing along the forearm the forearm volume can be reconstructed thereby providing information regarding the movement of that body part and other parts of the body.

With reference to FIG. 3, the signals measured at the receiving antennas 340 are used to provide volumetric change of the forearm by using dynamic cross-sectional contours based on the measured signals. The measured signals are used to provide reconstructed contours are shown in FIGS. 4-6.

When the wearable 300 is located on the forearm, motion and position related to the movement of the hands can be determined. Furthermore, motion and position related to the arm and other parts of the body that is reflected in the deformation of the skin and the volume reflected by the deformation (e.g. via localized deforming sensing) and the movement of the musculature, ligaments, circulatory system, etc. can also be ascertained from the wearable 300.

In an embodiment, the wearable is placed on the upper part of the arm. Motion and position related to movement and/or deformation within the shoulder area, hand area, neck area and other parts of the body that are able to be discerned from the positioning there are determined. In an embodiment, the wearable is placed on the upper part of the leg. Motion and position related to movement and/or deformation within the upper leg area, shin area, foot and ankle area, waist area, and other parts of the body that are able to be discerned from the positioning there are determined. In an embodiment, the wearable is placed on the shin area. Motion and position related to movement and/or deformation within the shin area, upper leg area, foot area and other parts of the body that are able to be discerned from the positioning there are determined. In an embodiment, the wearable is placed on the ankle area. Motion and position related to movement and/or deformation within the ankle area, shin area, upper leg area, foot area and other parts of the body that are able to be discerned from the positioning there are determined. In an embodiment, the wearable is placed on the chest area. Motion and position related to movement and/or deformation within the chest area, arm area, neck area, leg area and other parts of the body that are able to be discerned from the positioning there are determined. In an embodiment, the wearable is placed on the forehead. Motion and position related to movement and/or deformation of the forehead, face area, and other parts of the body that are able to be discerned from the positioning there are determined. It is contemplated that other embodiments and placements can be used in order to determine movement within other areas of the body In an embodiment, the sensing system is implemented in a wearable placed on the ankle. The placement of the sensing system's transmitting antennas and receiving antennas to correlate with musculature, bone, tendon and/or ligament activity that determine activities of the foot activity provides enhanced measurements of the foot activity. In an embodiment, the sensing system is implemented in a wearable placed on the arm. The placement of the sensing system's transmitting antennas and receiving antennas to correlate with musculature, bone, tendon and/or ligament activity that determine activities associated with the arm provides enhanced measurements of arm activity. In an embodiment, the sensing system is implemented in a sensing device placed on the chest. The placement of the sensing system's transmitting antennas and receiving antennas to correlate with musculature, bone, tendon and/or ligament activity that determine activities associated with the chest (e.g., breathing, heart rate, etc.) provides enhanced measurements of the associated chest activity. In an embodiment, the pressure adaptive sensor system is implemented in a wearable placed on the leg. The placement of the sensing system's transmitting antennas and receiving antennas to correlate with musculature, bone, tendon and/or ligament activity that determine activities associated with the leg provides enhanced measurements of leg activity. In an embodiment, the sensing system is implemented in a wearable placed on the head. The placement of the sensing system's transmitting antennas and receiving antennas to correlate with musculature, bone, tendon and/or ligament activity that determine activities associated with the head provides enhanced measurements of facial activity and head motion. In an embodiment, the sensing system is implemented in a wearable placed on the neck. The placement of the sensing system's transmitting antennas and receiving antennas to correlate with musculature, bone, tendon and/or ligament activity that determine activities associated with the neck provides enhanced measurements of vocalization, breathing, and other associated activities. In an embodiment, the pressure adaptive sensing system is implemented in a wearable placed on the waist. The placement of the sensing system's transmitting antennas and receiving antennas to correlate with musculature, bone, tendon and/or ligament activity that determine activities associated with the waist provide enhanced determination of movement and other associated activities. In an embodiment, the sensing system is implemented in a wearable placed on the hand. The placement of the sensing system's transmitting antennas and receiving antennas to correlate with musculature, bone, tendon and/or ligament activity that determine activities associated with the hand provides enhanced determination of fine hand movement. In an embodiment, the sensing system is implemented in a wearable placed on the foot. The placement of the sensing system's transmitting antennas and receiving antennas to correlate with musculature, bone, tendon and/or ligament activity that determine activities associated with the foot provides enhanced determination of fine foot movement.

An aspect of the disclosure is a wearable sensing system. The wearable sensing system comprises a substrate formed of a material adapted to fit to a body part at least one transmitting antenna operably connected to the substrate, wherein the transmitting antenna is adapted to transmit at least one signal; at least one receiving antenna adapted to receive the at least one signal, wherein the receiving antenna is operably connected to the substrate; and a signal processor adapted to process signals received by the at least one receiving antenna, wherein the signals received are processed in order to determine movement of a portion of a body, wherein the movement of a portion of the body is determined by determining localized pressure deformation of skin proximate to the substrate so as to reconstruct volumetric changes of the body part.

Another aspect of the disclosure is a method for sensing movement of a body part. The method comprising placing a substrate proximate to a body part, wherein operably connected to the housing is at least one transmitting antenna adapted to transmit signals; at least one receiving antenna adapted to receive signals, and a processor adapted to process measurements of signals received by the at least one receiving antenna, wherein processed measurements are used to determine movement proximate to the body part; wherein processed signals are used in order to determine movement of a portion of the body, wherein the movement of a portion of the body is determined by determining localized pressure deformation of skin proximate to the substrate so as to reconstruct volumetric changes of the body part; receiving at least one signal at the at least one receiving antenna; processing the at least one signal received; and determining movement of the portion of the body using the processed at least one signal received.

While the invention has been particularly shown and described with reference to a preferred embodiment thereof, it will be understood by those skilled in the art that various changes in form and details may be made therein without departing from the spirit and scope of the invention.

The invention claimed is:

1. A wearable sensing system comprising:
a substrate formed of a material adapted to fit to a body part;
at least one transmitting antenna operably connected to the substrate, wherein the transmitting antenna is adapted to transmit at least one signal;
at least one receiving antenna adapted to receive the at least one signal, wherein the receiving antenna is operably connected to the substrate; and
a signal processor adapted to process signals received by the at least one receiving antenna, wherein the signals received are processed in order to determine movement of a portion of a body, wherein the movement of a portion of the body is determined by determining localized pressure deformation of skin proximate to the substrate so as to reconstruct volumetric changes of the body part.

2. The wearable sensing system of claim 1, wherein the wearable sensing system is placed on a forearm.

3. The wearable sensing system of claim 1, wherein the material is a neoprene based material.

4. The wearable sensing system of claim 1, wherein the at least one signal is infused into the body part.

5. The wearable sensing system of claim 1, wherein the at least one receiving antenna is one of a plurality of receiving antennas.

6. The wearable sensing system of claim 1, wherein the at least one transmitting antenna transmits a plurality of signals, each signal transmitted orthogonal to each other signal transmitted during a time interval.

7. The wearable sensing system of claim 6, wherein each signal is frequency orthogonal to each other signal transmitted during a time interval.

8. The wearable sensing system of claim 1, wherein the at least one signal received is processed using a Fast Fourier Transform.

9. The wearable sensing system of claim 1, wherein the at least one transmitting antenna is one of a plurality of transmitting antennas.

10. The wearable sensing system of claim 1, wherein the determining of localized pressure deformation of skin proximate to the substrate comprises forming cross sections of the body part.

11. A method for sensing movement of a portion of a body comprising:
placing a substrate proximate to a body part, wherein operably connected to the substrate is at least one transmitting antenna adapted to transmit signals; at least one receiving antenna adapted to receive signals, and a processor adapted to process measurements of signals received by the at least one receiving antenna, wherein processed measurements are used to determine movement proximate to the body part; wherein processed signals are used in order to determine movement of a portion of the body, wherein the movement of a portion of the body is determined by determining localized pressure deformation of skin proximate to the substrate so as to reconstruct volumetric changes of the body part;
receiving at least one signal at the at least one receiving antenna;
processing the at least one signal received; and
determining movement of the portion of the body using the processed at least one signal received.

12. The method of claim 11, comprising placing the wearable on a forearm.

13. The method of claim 11, wherein the material is a neoprene based material.

14. The method of claim 11, comprising infusing the at least one signal is infused into the body part.

15. The method of claim 11, wherein the at least one receiving antenna is one of a plurality of receiving antennas.

16. The method of claim 11, wherein the at least one transmitting antenna transmits a plurality of signals, each signal transmitted orthogonal to each other signal transmitted during a time interval.

17. The method of claim 16, wherein each signal is frequency orthogonal to each other signal transmitted during a time interval.

18. The method of claim 11, wherein the at least one signal received is processed using a Fast Fourier Transform.

19. The method of claim 11, wherein the at least one transmitting antenna is one of a plurality of transmitting antennas.

20. The method of claim 11, wherein determining localized pressure deformation of skin proximate to the substrate comprises forming cross sections of the body part.

* * * * *